United States Patent [19]
Štraus

[11] Patent Number: 5,667,505
[45] Date of Patent: Sep. 16, 1997

[54] METHOD OF CARRYING OUT CRYOSURGICAL INTERVENTIONS AND DEVICE FOR THIS METHOD

[75] Inventor: Jaroslav Štraus, Prague, Czech Rep.

[73] Assignee: SMT spol. s.r.o., Czech Rep.

[21] Appl. No.: 307,666

[22] PCT Filed: Mar. 22, 1993

[86] PCT No.: PCT/CZ93/00004
  § 371 Date: Sep. 22, 1994
  § 102(e) Date: Sep. 22, 1994

[87] PCT Pub. No.: WO93/18714
  PCT Pub. Date: Sep. 30, 1993

[30] Foreign Application Priority Data

Mar. 24, 1992 [CZ] Czech Rep. .................... 885-92

[51] Int. Cl.$^6$ .................................................. A61B 17/36
[52] U.S. Cl. .................. 606/24; 606/20; 606/22; 606/25
[58] Field of Search ............................ 606/20–26

[56] References Cited

U.S. PATENT DOCUMENTS

| | | | |
|---|---|---|---|
| 3,439,680 | 4/1969 | Thomas, Jr. ............................ | 606/24 |
| 4,345,598 | 8/1982 | Zobac et al. ............................ | 606/24 |
| 4,860,744 | 8/1989 | Johnson et al. ........................ | 606/31 |
| 5,139,496 | 8/1992 | Hed ........................................ | 606/24 |
| 5,207,674 | 5/1993 | Hamilton ................................ | 606/23 |
| 5,334,181 | 8/1994 | Rubinsky et al. ...................... | 606/26 |

Primary Examiner—Angela D. Sykes
Assistant Examiner—Michael Peffley
Attorney, Agent, or Firm—Burns, Doane, Swecker & Mathis, L.L.P.

[57] ABSTRACT

A method of carrying out cryosurgical interventions includes cooling biological tissue at a rate of at least 180 K/min to a temperature of −190° C. to −160° C., subsequently rewarming the biological tissue at a rate of 100 to 240 K/min to a temperature of −70° C. to −20° C. with a subsequent rewarming at a rate of 10 to 25 K/min to a temperature of −5° C. to +5° C., and further rewarming the biological tissue up to body temperature. The total time of the controlled rewarming of the biological tissue is shorter than 5 minutes. An apparatus for carrying out the method of cryosurgical interventions includes a container of cooled medium an operating instrument, and a control unit for controlling the cooling and subsequent rewarming of biological tissue. The control unit includes a microprocessor coupled to electronic switches and a measuring unit.

17 Claims, 2 Drawing Sheets

METHOD OF CARRYING OUT CRYOSURGICAL INTERVENTIONS AND DEVICE FOR THIS METHOD

TECHNICAL FIELD

The invention concerns the method of carrying out cryosurgical interventions based on the destruction of the pathological tissue consisting of freezing the biological tissue below −25° C. with its subsequent rewarming up to the body temperature and the device for carrying out this method consisting of operating apparatus with a built in container of cooling medium and operating instrument and control unit.

BACKGROUND OF THE INVENTION

In the destruction of the pathological tissue by the local deep undercooling for the therapeutic treatment of benign as well as malignant tumors in the proctology, gynecology, oncological surgery, etc., the biological tissue has been yet exposed to the action of low temperature below −25° C. After that, the biological tissue is rewarmed up to the initial body temperature. In the still known methods rapid freezing with subsequent rewarming up at a comparable speed is performed.

The disadvantage of this known procedure is particularly a too high speed when rewarming the tissue up to the initial temperature. For achieving a reliable cryodestruction, in the literature, as well as in accordance with experience in practice rapid cooling is recommended down to temperatures below −25° C. at a rate of about 200 K/min or above with a subsequent moderate rewarming up to the body temperature at a rate of 10 to 20 K/min. With respect to the necessary rewarming rate, the whole operation would be very time consuming and this approach is not feasible with respect to the fact that the intervention calls for a high degree of the concentration.

For the methods mentioned, devices have been yet known consisting of an operation apparatus with a built in container of the cooling medium, most typically liquid nitrogen. To the operation apparatus, an operation instrument is attached having at its end a heat exchanger or applicator arranged for fitting operating tips.

This device makes possible only rapid cooling and comparably rapid rewarming of the tissue. Thus, the drawback is in the impossibility of a suitable continuous control of the cooling and particularly rewarming rates. The temperature control is implemented by the maximum rate given by the heating power of relevant heat exchangers of the operating apparatus and by their instantaneous thermal load. A further disadvantage is in the impossibility of checking proper fitting of tips to the operation instrument and thus also the impossibility of checking the necessary contact between the operation tip and tissue. The impossibility is also disadvantageous of the preliminary determination of the cooling power in the still existing devices.

SUMMARY OF THE INVENTION

The above mentioned disadvantages are to a considerable extent avoided by a method of performing the cryosurgical intervention consisting of cooling the biological tissue below −25° C. with its subsequent rewarming to the body temperature in accordance with the invention. Its principle is in that the contact area of the biological tissue is cooled down at a rate of at least 180 K/min to −190° to −160° C., after that it is rewarmed at a rate of 100 to 240 K/min to −70° to −20° C. Then the contact area of the biological tissue is rewarmed at a rate of 10 to 25 K/min to −5° to +5° C. with a subsequent continuation of the rewarming procedure up to the body temperature. A considerable advantage of this method is that the total time of the controlled rewarming procedure is shorter than 5 min, which can be provided.

For perfoming the described method it is suitable to use the device consisting of an operation apparatus with a built in container of the cooling medium and operation instrument, and of the controlling unit in accordance with the invention. Its principle is that the control unit is formed by a controlling microprocessor coupled to electronic switches of an electromagnetic valve of heat exchanger, a heater of the heat exchanger, an additional heater of outlet gases and an additional heater of a pressurized heating. The controlling microprocessor is further coupled to a measuring unit connected with the heat exchanger thermometer, further thermometer of the outlet gas heater, manometer of the container, indicator of the cooling medium level and a further thermometer of the pressurizing heating. The controlling microprocessor can be preferably connected to a power supply and memory with its further connection to a display unit and keyboard.

The method described makes possible a high-quality cryosurgical intervention in a suitable time interval while adhering to all the cryobiological requirements.

The device corresponding to the invention makes it possible to measure the freezing power of the coolant prior to the intervention itself. Prior to the intervention, it is also possible to automatically establish the quality of the thermal contact between the heat exchanger-applicator and operating tip. In the course of the intervention it is possible to automatically check the quality of the thermal contact between the operating tip and contact area of the biological tissue for possible ocurrence of breaking off of the operation tip from the contact area of the tissue, i.e. sudden deterioration of the thermal contact by the action of microscopic cracks between the operating tip and contact area of the tissue. The further advantage is a possibility of automatically providing tissue rewarming in accordance with cryobiological requirements after the cooling, i.e. rewarming at a rate of at most 10 to 25 K/min in a temperature interval of −25° to 0° C. The total rewarming time will not exceed 4 min, which is a suitable time delay from the standpoint of the concentration for the given intervention.

BRIEF DESCRIPTION OF THE DRAWINGS

The device for carrying out the cryosurgical intervention is described in detail with the help of a drawing of a particular implementation, wherein.

DETAILED DESCRIPTION OF THE PREFERRED EMBODIMENTS

One example of performing the cryosurgical intervention consisting in cooling the biological tissue below −25° C. with its subsequent rewarming to the body temperature was based on the fact that the contact area of the biological tissue was cooled down at a rate of 200 K/min to a temperature of −180° C. After that it was rewarmed at a rate of 150 K/min to −50° C. with further rewarming at a rate of 20 K/min to +5° C. After that, continuous rewarming occured up to the body temperature at a rate of 200 K/min. At a contact area of 25 mm in diameter, the biological tissue of a diameter of about 28 mm and depth 4 mm was involved. The total rewarming time was shorter than 4 min.

In a further case, the contact area of the biological tissue was cooled down at a rate of 3 000 K/min to −170° C. and this temperature was kept for 45 s. The biological tissue was then rewarmed in the same way as in the first case. For a contact area of 5 mm in diameter, the biological tissue of a diameter of about 7 mm and depth of 3 mm was involved.

In a further particular case, the contact area of the biological tissue was cooled down at a rate of 600 K/min to −180° C., this temperature being kept for 30 s. After that, the biological tissue was rewarmed at a rate of 200 K/min to −30° C. with a subsequent rewarming in the same way as in the above mentioned cases. For a contact area of 12 mm in diameter, the biological tissue of a diameter of about 15 mm and depth of 4 mm was involved.

In the last particular case, the contact area of the biological tissue was cooled down at a rate of 200 K/min to −160° C. and it was kept at this temperature for 120 s. The biological tissue was then rewarmed in the same way as in the first example. For a contact area of 25 mm in diameter, with outputs arranged into seven points, 14 mm long and 3 mm in diameter, the biological tissue of a diameter of about 28 mm and depth of 17 mm was involved.

Figure 1:
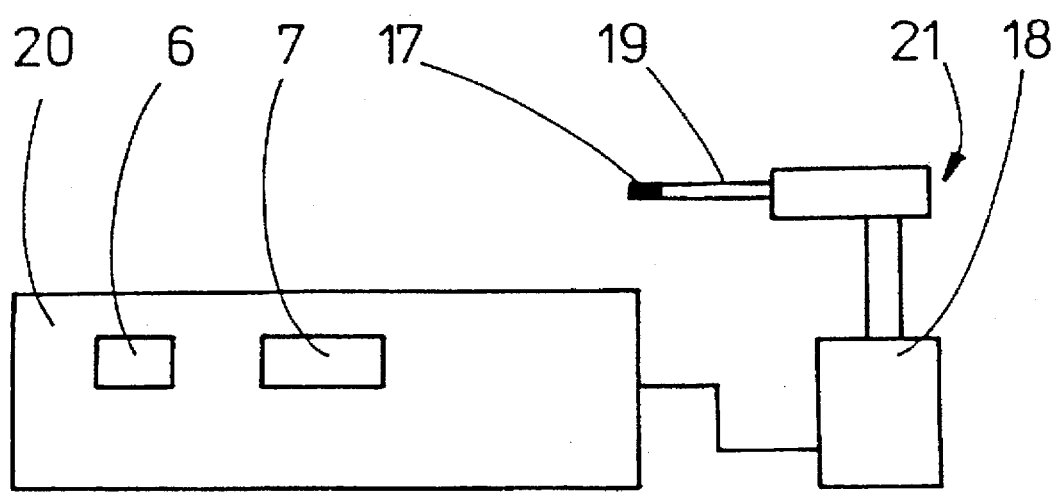
FIG. 1 is a schematic diagram of the device according to the invention.
Figure 2:
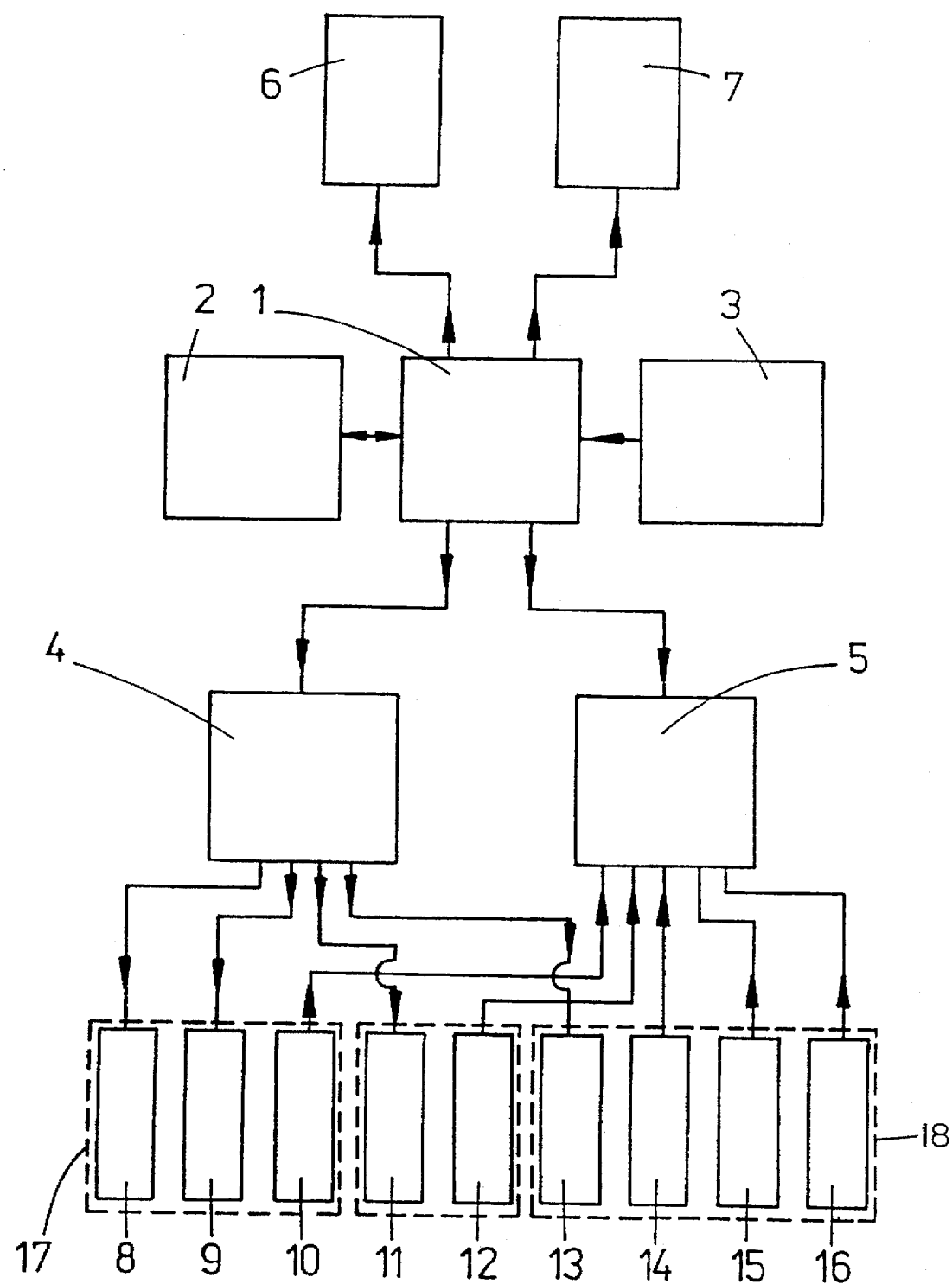
FIG. 2 is a schematic diagram of the connections of particular elements of the control unit of the device of FIG. 1.

With reference to FIG. 1, a device for carrying out this method consists of an operating apparatus 21 with a built in container 18 of the cooling medium and operating instrument 19 and control unit 20. With reference to FIG. 2, the control unit 20 consists of a control microprocessor 1, attached to a block 4 of electronic switches, which are connected with an electromagnetic valve 8 of the heat exchanger 17, a heater 9 of the heat exchanger 17, an additional heater 11 of the outlet gases, and an additional heater 13 of the pressurized container 18. The control microprocessor 1 is further coupled. Microprocessor 1 is further coupled to a measuring unit 5, connected to a thermometer 10 of the heat exchanger 17, further thermometer 12 of the heater of outlet gases, manometer 14 of the container, level indicators 15 and a further thermometer 16 of the pressurized heating. The controlling microprocessor 1 is coupled to an independent power supply 3 and external memory 2 and it is further connected to the display unit 6 and keyboard 7.

Before carrying out the operating intervention itself, the freezing power of the equipment for the cryosurgical intervention and the quality of the thermal contact between the heat exchanger 17 and tip is checked. In the course of the operation intervention, it is possible to control the rewarming rate in accordance with the dependence recommended. The cooling power should be evaluated depending on the heat exchanger 17 cooling course expressing the time dependence of the heat exchanger 17 temperature at the cooling stage without the contact with the tissue and without the passive tip. For this evaluation, two suitably chosen points of the course are sufficient $(t_1, T_1)$ and $(t_2, T_2)$, determining the rate of cooling the heat exchanger 17 and the cooling power is determined from the known capacity of the heat exchanger 17. For achieving as precise measurement as possible and for simultaneous checking of the function of the instrument 19 even at the lowest temperature, it is suitable to choose the origin of cooling as the first point (0,+36) and (t,−185) as the second point. Instead of the value of the cooling power, it is also possible to directly present the measured cooling rate. In practice, this means that after pressing the switch for testing the power the time measurement is started and freezing is switched on, i.e. the electromagnetic valve 8 is switched on and heater 9 of the heat exchanger 17 is switched off. After achieving the temperature chosen, for example −185° C., corresponding time is recorded and freezing is switched off. It is advantageous to wait for a certain time interval, for example one s, in order that the temperature in the heat exchanger 17 could be uniformly distributed and to use a steady state value after determining the cooling rate. The normal rewarming to the initial temperature is then adopted, i.e. the control of heating 9 of the exchanger is switched to +36° C.

Before starting the intervention itself, it is also possible to establish the quality of the thermal contact between the heat exchanger 17 and tip of the cryodevice. After pressing the button test, freezing is started, which means that the electromagnetic valve 8 is switched on and heater 9 of the heat exchanger 17 is switched off. After achieving a certain temperature recorded by a thermometer 10 of the heat exchanger 17, for example −30° C., the freezing process is terminated, the lowest achieved temperature $T_A$ is recorded and after a stabilization for about 10 s, temperature $T_B$ is measured. Their mutual ratio is a measure of the quality of the thermal contact.

However, in order that comparable data could be obtained for all the sizes of the tips, the thermal capacity of the tip together with the heat exchanger 17 is further measured during heating with a defined heating power for the whole time. From these data, a number in the interval of 0 to 100 is obtained, characterizing the quality of the thermal contact.

During the implementation of the intervention itself, the tip can be broken off from the tissue, which is manifested by a subsequent deterioration of the thermal contact resulting from the action of microscopic cracks between the tip and tissue. This breaking off exerts an adverse effect on the cooling rate and thus also on the quality of the cryodestruction. This is manifested by a reduced depth of freezing and lower probability of the tumorous cell destruction. In addition the healing process is also deteriorated. Thus, it is necessary to check the possible occurrence of this breaking off. This checking is performed by following the time course of the heat exchanger 17 in a regime with a controlled inlet of the coolant into the exchanger 17 after achieving a given exchanger 17 temperature. In the case of breaking off the tip, a sudden change of the nature of regulation cycles occurs. The cooling course is then steeper and, in contrast to this, the course of the rewarming process is less steep, the resulting regulation period being longer after breaking off the tip. The change of the course is evaluated and breaking off of the tip from the tissue is signalled. In this case it is possible to interrupt the power, to wait for the tissue and tip heating and to repeat the whole operation intervention.

It is of a high importance to adhere to the recommended tissue rewarming rate in a range of temperature of −25° to 0° C., in the whole volume of the tissue to be destroyed as far as possible, provided that the total time of controlled rewarming does not exceed four min. The control of the rewarming rate is provided with the help of the microprocessor 1 controlling electronic switches 4 and output data are shown on the display 6.

Industrial applicability

The method of performing cryosurgical interventions and device for performing this method in accordance with the invention will find its application particularly in the treatment of pathological formations in the proctology, gynecology and oncological surgery and further in dermatology, orofacial surgery, otrinolaringology, pneumology, urology, cardiosurgery, etc.

I claim:

1. A device for performing cryodestruction of tissue comprising:
   an operating instrument including a heat exchanger having a first heater, a valve, and a first temperature sensor;
   a pressurized container of cooling medium for delivering cooling medium to the operating instrument, the pressurized container including a second heater, a second temperature sensor, and a pressure sensor;
   an outlet gas heating means including a third heater, and a third temperature sensor; and
   a controlling microprocessor coupled to electronic switches of the valve, and the first, second, and third heaters, said controlling microprocessor being further connected to a measuring unit coupled to the first, second, and third temperature sensors, and the pressure sensor, the controlling microprocessor providing means for varying a rewarming rate during rewarming of the tissue.

2. A device in accordance with claim 1, wherein the pressurized container further comprises a level indicator which is coupled to the measuring unit.

3. A device in accordance with claim 1, wherein the microprocessor further comprises means for controlling a speed of warming of the operating instrument.

4. A device in accordance with claim 1, wherein the microprocessor further comprises means for rewarming biological tissue at a rate of 100 to 240 K/min to a temperature of −70° C. to −20° C. and for further rewarming at a rate of 10 to 25 K/min to a temperature of −5° C. to +5° C.

5. A device in accordance with claim 1, wherein the microprocessor further comprises means for rewarming biological tissue at a rate of 100 to 240 K/min to a temperature of −70° C. to −20° C. and for further rewarming at a rate of 10 to 25 K/min to a temperature of −5° C. to +5° C., with said rewarming being achieved in a total time of less than 5 minutes.

6. A device in accordance with claim 1, wherein the pressurized container is attached to the operating instrument.

7. A device in accordance with claim 1, further comprising an operating tip for cooling tissue and means for automatically establishing a quality of a thermal contact between the heat exchanger and the operating tip prior to and during rewarming.

8. A device in accordance with claim 7, wherein the operating tip is removable from an operating end of the device which includes the heat exchanger and the temperature sensor of the heat exchanger.

9. A device in accordance with claim 1, further comprising means for measuring the freezing power of the cooling medium prior to a cryosurgical intervention.

10. A method of carrying out cryosurgical interventions consisting of cooling biological tissue below −25° C. with a subsequent rewarming to body temperature, comprising the steps of cooling down the contact area of the biological tissue at a rate of at least 180 K/min to a temperature of −190° to −160° C., subsequently rewarming the biological tissue at a rate of 100 to 240 K/min to a temperature of −70° to −20° C. with a subsequent rewarming at a rate of 10 to 25 K/min to a temperature of −5° to +5° C. and further rewarming of the biological tissue up to the body temperature, with the total time of the controlled rewarming of the biological tissue being shorter than 5 minutes.

11. A hand held device for carrying out cryosurgical interventions, comprising:
    an operating instrument having an operating tip for applying cryogenic energy to tissue;
    a heat exchanger and a heater of the heat exchanger, the heater and heat exchanger being located at the operating tip;
    a container of cooling medium mounted on the operating instrument for supplying the cooling medium to the operating tip, the container including an container heater;
    a heater of outlet gasses;
    a control unit, said control unit comprising a controlling microprocessor coupled to electronic switches of the heat exchanger, of the heater of the heat exchanger, of the heater of outlet gases and of the container heater, said controlling microprocessor being further connected to a measuring unit coupled to a thermometer of the heat exchanger, to a further thermometer of the heater of outlet gases, to a manometer of the container, to level indicators of the container and to a further thermometer of the container, the controlling unit providing means for varying a rewarming rate during rewarming of the tissue.

12. A device in accordance with claim 11, wherein the controlling microprocessor is coupled to an independent power supply and to external memory and wherein the controlling microprocessor is further connected to a display unit and keyboard.

13. A device in accordance with claim 11, wherein the controlling microprocessor includes means for rewarming biological tissue at a rate of 100 to 240 K/min to a temperature of −70° C. to −20° C. and for further rewarming at a rate of 10 to 25 K/min to a temperature of −5° C. to +5° C.

14. A device in accordance with claim 11, wherein the controlling microprocessor includes means for rewarming biological tissue at a rate of 100 to 240 K/min to a temperature of −70° C. to −20° C. and for further rewarming at a rate of 10 to 25 K/min to a temperature of −5° C. to +5° C., with said rewarming being achieved in a total time of less than 5 minutes.

15. A device in accordance with claim 11, further comprising means for automatically establishing a quality of a thermal contact between the heat exchanger and the operating tip prior to and during rewarming.

16. A device in accordance with claim 15, wherein the operating tip is removable from an operating end of the device which includes the heat exchanger and the thermometer of the heat exchanger.

17. A device in accordance with claim 11, further comprising means for measuring the freezing power of the cooling medium prior to a cryosurgical intervention.

* * * * *